United States Patent [19]

Cragoe, Jr. et al.

[11] Patent Number: 4,465,850

[45] Date of Patent: Aug. 14, 1984

[54] TREATMENT OF BRAIN INJURY DUE TO GRAY MATTER EDEMA WITH (INDANYLOXY) BUTANOIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 430,891

[22] Filed: Sep. 30, 1982

Related U.S. Application Data

[63] Continuation of Ser. No. 291,982, Aug. 11, 1982, abandoned, which is a continuation-in-part of Ser. No. 183,546, Sep. 2, 1980, abandoned.

[51] Int. Cl.³ ............................................. C07C 69/76
[52] U.S. Cl. .................................. 560/053; 562/462; 424/308; 424/317
[58] Field of Search ................... 560/56, 53; 562/466, 562/462; 424/308, 317

[56] References Cited

U.S. PATENT DOCUMENTS 4,070,539 1/1928 Cragoe, Jr. ........................... 560/56

Primary Examiner—Paul J. Killos
Attorney, Agent, or Firm—Thomas E. Arther; Mario A. Monaco

[57] ABSTRACT

The invention relates to the treatment and prevention of injury to the gray matter of the brain and to the spinal chord due to accidents, ischemic stroke, cardiac arrest, arrested breathing, Reye's syndrome and hydrocephalus by the administration of (indanyloxy)butanoic acids, their derivatives, analogs and salts thereof.

32 Claims, No Drawings

TREATMENT OF BRAIN INJURY DUE TO GRAY MATTER EDEMA WITH (INDANYLOXY) BUTANOIC ACIDS

This is a continuation of application Ser. No. 291,982, filed Aug. 11, 1982, which in turn is a continuation-in-part of application Ser. No. 183,546, filed Sept. 2, 1980, both which have been abandoned.

BACKGROUND OF THE INVENTION

Traumas to the brain caused by outside physical forces acting on the skull or spinal chord (hereinafter, head or spine injury), ischemic stroke, and hydrocephalus are all characterized by edema and resultant swelling. The standard treatment has been the administration of steroids, because of their known antiinflammatory activity or procedures such as the insertion of a shunt in the case of progressive hydrocephalus. Diuretics have not been used to treat brain and spinal chord edema partly because the blood-brain barrier prevents adequate concentrations of the diuretics from reaching brain cells. Thus, any decrease in edema following diuretic administration would be a secondary or independent effect resulting from general electrolyte loss and resultant dehydration of the rest of the body. Such dehydration would be inappropriate to someone with a traumatized brain or spinal cord.

Long, et al., *Dynamics of Brain Edema*, pp. 293–300, Springer-Verlag (1976) described the use of the diuretics furosemide and acetazolamide for the treatment of certain models of brain edema in cats.

Bourke, et al., *Brain Research*, 105 (1976) 309–323 described the effect of the diuretics ethacrynic acid and acetazolamide on swelling of monkey cerebrocortical slices. Nelson, et al. *Neural Trauma*, edited by A. J. Popp et al., Raven Press, New York, 1979, p. 297, have described the use of ethacrynic acid in brain injury.

SUMMARY OF THE INVENTION

The invention comprises the treatment of persons with gray matter edema. This edema can be the result of any of a variety of causes; for example, from external physical forces such as a blow to the head, neck or spine, a motor vehicle accident, or a fall, from ischemic stroke, from hydrocephalus, or from radiation. The treatment comprises administering to such a person an effective amount of a compound of the formulae:

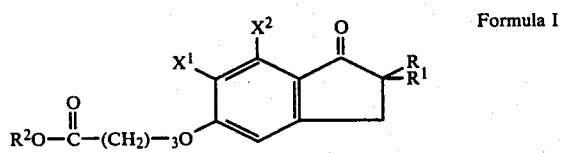

Formula I where
X$^1$ and X$^2$ are halo;
R is lower alkyl of from 1 to 6 carbon atoms;
R$^1$ is hydrogen, lower alkyl of 1–4 carbon atoms; cycloalkyl of 3 to 6 carbon atoms, lower cycloalkylloweralkyl 4–7 carbon atoms; and phenyl;
R$^2$ is hydrogen, lower alkyl of 1–5 carbon and carboxy lower alkyl of 2–6 carbon atoms.

Since the 2-carbon atom in the molecule is asymmetric, the compounds of the invention where R and R$^1$ are different are racemic; however, these compounds can be resolved, so that the invention includes the pure enantiomers. In addition, in some instances, the group represented by R$^2$ includes an asymmetric carbon atom. Thus, these molecules may contain two asymmetric carbon atoms and now can consist of two diastereomers, each of which consists of two enantiomers. The invention includes each diastereomer and their enantiomers whenever they exist.

Although the invention involves novel (indanyloxy)-butanoic acids it also includes the obvious analogs, their corresponding esters, salts and their anhydrides, amides, hydrazides, guanidides and the like.

A particular advantage of the compounds of the invention is that they belong to a chemical subgroup which possess maximal anti-brain edema activity and minimal renal (diuretic) activity.

A further aspect of this invention is the concomitant administration of a compound of formula I or II with an antiinflammatory steroid or barbiturate for the treatment of gray matter edema of the brain or spinal chord.

DETAILED DESCRIPTION OF THE INVENTION

Some of the compounds of formulae I are known, and are described in U.S. Pat. No. 4,081,554 issued Mar. 28, 1978.

By alkyl is meant both straight- and branched-chain alkyl such as methyl, ethyl, n-butyl, sec-butyl, iso-butyl, t-butyl, pentyl and the like. Cycloalkyl includes cyclopropyl, cyclobutyl, cyclopentyl, and cyclohexyl. By halo is meant fluoro, chloro, and bromo.

As mentioned previously, the use of the enantiomeric forms of the compound of formulae I is included within the scope of this invention. It is to be noted that one enantiomer generally possesses most or all the anti-brain edema activity expressed by the racemic compound.

Preferred compounds of formulae I are those where R is alkyl of one to six carbons.

Other preferred compounds of formula I are those where X$^1$ and X$^2$ are both chloro, R$^1$ is cyclopentyl, and R$^2$ is H.

Other preferred compounds of formula I are those where R$^2$ is 1-carboxy-1-methylethyl.

A preferred compound is 4-[(6,7-dichloro-2-cyclopentyl-2,3-dihydro-2-methyl-1-oxo-1H-inden-5-yl)oxy]-butanoic acid.

Another preferred compound is the (+) enantiomer of 4-[(6,7-dichloro-2-cyclopentyl-2,3-dihydro-2-methyl-1-oxo-1H-inden-5-yl)oxy]butanoic acid.

Another preferred compound is 4-[(6,7-dichloro-2-cyclopentyl-2-ethyl-2,3-dihydro-1-oxo-1H-inden-5-yl)oxy]butanoic acid.

Another preferred compound of the invention is 4-[(6,7-dichloro-2-cyclopentyl-2,3-dihydro-1-oxo-2-propyl-1H-inden-5-yl)oxy]butanoic acid.

Another preferred compound of the invention is 4-[(2-butyl-6,7-dichloro-2-cyclopentyl-2,3-dihydro-1-oxo-1H-inden-5-yl)oxy]butanoic acid.

Another preferred compound of the invention is the (+) enantiomer of 4-[(2-butyl-6,7-dichloro-2-cyclopentyl-2,3-dihydro-1-oxo-1H-inden-5-yl)oxy]butanoic acid.

Another preferred compound is the (−) enantiomer of 4-[(2-butyl-6,7-dichloro-2-cyclopentyl-2,3-dihydro-1-oxo-1H-inden-5-yl)oxy]-butanoic acid.

Another preferred compound of the invention is the (+) enantiomer of 1-carboxy-1-methylethyl 4-[(6,7-dichloro-2-cyclopentyl-2,3-dihydro-2-methyl-1-oxo-1H-inden-5-yl)oxy]butanoate.

Another preferred compound of the invention is the (+) enantiomer of 1-carboxy-1-methylethyl [(2-butyl-6,7-dichloro-2-cyclopentyl-2,3-dihydro-1-oxo-1H-inden-5yl)oxy]butanoate.

Another preferred compound of the invention is the (−) enantiomer of 1-carboxy-1-methylethyl [(2-butyl-6,7-dichloro-2-cyclopentyl-2,3-dihydro-1-oxo-1H-inden-5-yl)oxy]butanoate.

Included within the scope of this invention is the use of the salts, esters, and amide derivatives of formulae I compounds which are prepared by conventional methods well known to those skilled in the art, i.e., reaction of the appropriate (indanyloxy)butanoic acid and selected alcohol with dicyclohexylcarbodiimide. In addition, the ester derivatives may be prepared by the reaction of the formulae I compounds of this invention with an alcohol, for example, with a hydroxyalkanoic acid in the presence of an acid catalyst.

Esters, such as the 1-carboxy-1-methylethyl esters (II) can be prepared by heating the appropriate acylating agent (III or IV) with 2-hydroxy-isobutyric acid.

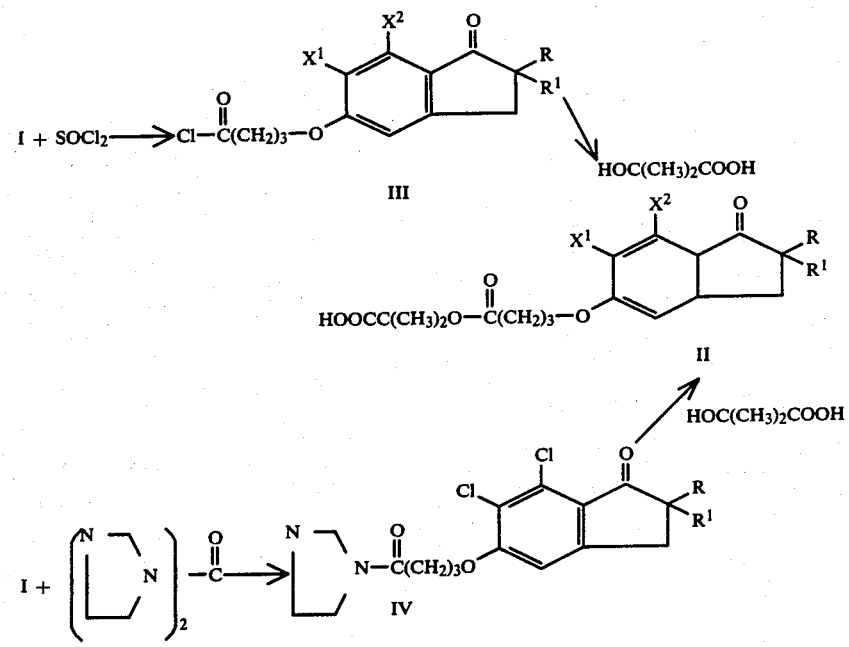

The intermediate III can be made by warming I with SOCl$_2$ in an enert solvent and IV can be synthesized by treating I with 1,1'-carbonyldiimidazole in a solvent such as tetrahydrofuran.

The amide derivatives may be prepared by converting a formulae I compound to its corresponding acid chloride by treatment with thionyl chloride followed by treating said acid chloride with ammonia, an appropriate mono-lower alkyl amine, di-lower alkyl amine or a hetero amine, such as piperidine, morpholine and the like, to produce the corresponding amide compound. These and other equivalent methods for the preparation of the salts, esters, and amide derivatives of the instant products will be apparent to one having ordinary skill in the art and to the extent that said derivatives are both non-toxic and pharmacologically acceptable, said derivatives are the functional equivalent of the corresponding compounds of formulae I.

The preferred salts are: sodium, potassium, ammonium, ethanolamine, diethanolamine, triethanolamine, N-methylpiperazine, piperazine, cyclohexylamine, N-methylglucamine, N-methylglucosamine, tetramethylammonium, and the like.

Inasmuch as there is a wide variety of symptoms and severity associated with gray matter edema, particularly when it is caused by blows to the head or spinal chord, the precise treatment protocol is left to the practitioner. It is up to the practitioner to determine the patient's response to treatment and to vary the dosages accordingly. A recommended dosage range is from 1 μg to 2 mg/kg of body weight as a primary dose and a sustaining dose of half to equal the primary dose, every 12 to 24 hours.

The compounds of this invention can be administered by a variety of established methods, including intravenously, intramuscularly, subcutaneously, and orally. As with dosage, the precise mode of administration is left to the discretion of the practitioner.

Since some of the compounds used for this invention have diuretic properties which may vary in intensity from compound to compound, it is recommended that the person under therapy receive an intravenous infusion equivalent to the lost water and electrolyte. Here again the rate of infusion and the solutions used are left to the discretion of the practitioner.

Studies on human pathological tissues have revealed that ischemic insult to the brain is a major concomitant of head injury.

Recent studies in experimental head injury by R. S. Bourke et al. (R. S. Bourke, M. A. Daze and H. K. Kimelberg, Monograph of the International Glial Cell Symposium, Leige, Belgium, Aug. 29-31, 1977 (in press) and references cited therein) and experimental stroke by J. H. Garcia et al. (J. H. Garcia, H. Kalimo, Y. Kamijyo and B. F. Trump, Virchous Archiv. B (1977), (in press) indicate that astroglial swelling, a secondary and potentially inhibitable process, is a fundamental pathophysiological response to ischemic/traumatic brain insult in both pathological disorders. Furthermore, astroglial swelling is believed to reduce oxygen available to neurons by prolongation of the oxygen diffusion pathway. Thus, the damage to cerebral grey matter may be far more extensive as a result of pathological events secondary to astroglial swelling than as a result of damage inflicted by the initial ischemic/traumatic insult. Consequently, it is of prime importance that the treatment commence as soon as possible after the initial trauma in order to minimize the brain cell damage and the possibility of death or permanent paralysis.

One aspect of this invention is the treatment of persons with gray matter edema by concomitant administration of compounds of formulae I or II or a pharmaceutically acceptable salt, ester, or amide thereof and of antiinflammatory steroids, and/or barbiturates. These steroids are of some, albeit limited, use in control of white matter edema associated with ischemic stroke and head injury. Steroid therapy is given according to established practice as a supplement to the compound of formula I as taught elsewhere herein.

The compounds of the invention generally are prepared by the synthetic methods described in U.S. Pat. No. 3,984,465. The examples which follow illustrate the products of the invention and the methods by which they are prepared. However, the examples are only illustrative and it will be apparent to those having ordinary skill in the art that all the products embraced by formula I, supra., also may be prepared in an analogous manner by substituting the appropriate starting materials for those set forth in the examples.

EXAMPLE 1

4-[(6,7-Dichloro-2-cyclopentyl-2,3-dihydro-2-methyl-1-oxo-1H-inden-5-yl)oxy]butanoic Acid

Step A:
2',3'-Dichloro-4-'methoxy-2-cyclopentylacetophenone 2,3-Dichloroanisole (57.8 g, 0.327 mole) is dissolved in dichloromethane (300 ml.) and cyclopentylacetyl chloride (52.7 g., 0.367 mole) is added. The solution is cooled to 5° C. and aluminum chloride (48.0 g. 0.36 mole) is added gradually over a one-hour period at 5° C. The mixture is stirred for two hours at 5° C. and at 20°–25° C. for 16 hours and then poured into 1 liter of ice water containing 150 ml. of 12N hydrochloric acid. The organic phase is separated and the aqueous phase is extracted with dichloromethane. The combined organic phases are washed first with a sodium chloride solution, then a 10% sodium hydroxide solution and again with sodium chloride solution and finally dried over magnesium sulfate. On evaporation of the solvent a brown solid is obtained which is crystallized from hexane to obtain 53.2 g. of 2',3'-dichloro-4'-methoxy-2-cylcopentylacetophenone, m.p. 60°–61.5° C.

Elemental analysis for $C_{15}H_{16}Cl_2O_2$: Calc.: C, 58.55; H, 5.62; Found: C, 58.72; H, 5.71.

Step B:
4-(2-Cyclopentyl-2-methyleneacetyl)-2,3-dichloroanisole 2,3-Dichloro-4-methoxy-2-cyclopentylacetophenone (51.6 g., 0.18 mole) is dissolved in dioxane (460 ml.) and paraformaldehyde (21.6 g., 0.72 mole) and concentrated sulfuric acid (9.65 g.) are added. The mixture is heated at 80°–85° C. for 20 hours. The dioxane is evaporated at reduced pressure. Water is added to the residual gum which then is extracted into ether. The ether extract is washed with water and dried over magnesium sulfate. The ether is evaporated and upon triturating the residue with hexane (5 ml.) there is obtained a solid that is crystallized from ligroin to obtain 4-(2-cylcopentyl-2-methyleneacetyl)-2,3-dichloroanisole (33.3 g.), m.p. 59°–63° C. Crystallization from butyl chloride affords a sample (m.p. 66°–67.5° C.) for analysis.

Elemental analysis for $C_{16}H_{16}Cl_2O_2$: Calc.: C, 60.21; H, 5.37; Found: C, 60.19; H, 5.42.

Step C:
6,7-Dichloro-2-cyclopentyl-2,3-dihydro-5-methoxy-1H-inden-1-one 4-(2-Cyclopentyl-2-methyleneacetyl)-2,3-dichloroanisole (33.3 g.) is dissolved in 98% sulfuric acid (150 ml.) and stirred at 20° C. for 1.5 hours. The solution then is added dropwise with stirring to ice water. The aqueous phase is decanted from the gummy product and fresh water is added. After 20 hours the gum solidifies and is crystallized from hexane-benzene (3:1) to obtain 6,7-dichloro-2-cyclopentyl-2,3-dihydro-5-methoxy-1H-inden-1-one, m.p. 116°–117° C.

Elemental analysis for $C_{16}H_{16}Cl_2O_2$: Calc.: C, 60.21; H, 5.37; Found: C, 60.29; H, 5.35.

Step D:
6,7-Dichloro-2-cyclopentyl-2,3-dihydro-5-methoxy-2-methyl-1H-inden-1-one 6,7-Dichloro-2-cyclopentyl-2,3-dihydro-5-methoxy-1H-inden-1-one (7.5 g., 0.025 mole) is dissolved in dry 1,2-dimethoxyethane (200 ml.) under nitrogen. Sodium hydride (57% in mineral oil; 1.16 g., 0.0275 mole) is then added and the mixture is stirred at 80° until evolution of hydrogen ceases (2 hours). The solution is cooled and methyl iodide (7.5 ml.) is added, the mixture is again brought to reflux and then cooled. Most of the 1,2-dimethoxyethane is evaporated and water is added to the residue which soon solidifies and is crystallized from methylcyclohexane and from ethanol-water (4:1) to obtain 3.4 g. of 5,6-dichloro-2-cyclopentyl-2,3-dihydro-5-methoxy-2-methyl-1H-inden-1-one, m.p. 109°–111.5° C.

Elemental analysis for $C_{17}H_{18}Cl_2O_2$: Calc.: C, 61.35; H, 5.79; Found: C, 61.71; H, 5.84.

Step E:
6,7-Dichloro-2-cyclopentyl-2,3-dihydro-5-hydroxy-2-methyl-1H-inden-1-one 6,7-Dichloro-2-cyclopentyl-2,3-dihydro-5-methoxy-2-methyl-1H-inden-1-one (3.4 g., 0.0109 mole) is added to dry heptane (180 ml.) and aluminum chloride (4.36 g., 0.0327 mole) is added. The mixture is refluxed for one hour and the heptane is decanted from the gummy residue which then is added to ice water (200 ml.) containing 12N hydrochloric acid (15 ml.). The solid that separates is crystallized from benzene to obtain 2.77 g. of 6,7-dichloro-2-cyclopentyl-2,3-dihydro-5-hydroxy-2-methyl-1H-inden-1-one, m.p. 190°–194° C.

Elemental analysis for $C_{16}H_{16}Cl_2O_2$: Calc.: C, 60.21; H, 5.37; Found: C, 60.43; H, 5.41.

Step F:
4-[(6,7-Dichloro-2-cyclopentyl-2,3-dihydro-2-methyl-1-oxo-1H-indene-5-yl)oxy]butanoic Acid A stirred mixture of 6,7-dichloro-2-cyclopentyl-2,3-dihydro-5-hydroxy-2-methyl-1H-inden-1-one (30.9 g., 0.1 mole), potassium carbonate (15.2 g., 0.11 mole) and ethyl 4-bromobutyrate (23.5 g., 0.11 mole) in DMF (200 ml.) is heated at 55°–60° C. for 2 hours, then treated with water (200 ml.) and 10N sodium hydroxide (40 ml.)

and heated at 95° C. for 2 hours. The reaction mixture is poured into ice water (500 ml.) containing conc. hydrochloric acid (50 ml.) extracted with ether which is washed with brine and dried over MgSO$_4$. The ether is evaporated at reduced pressure and the resultant oil crystallized from butyl chloride to give 16 g. of 4-[(6,7-dichloro-2-cyclopentyl-2,3-dihydro-2-methyl-1-oxo-1H-inden-5-yl)oxy]butanoic acid which melts at 154° C.

Analysis for C$_{19}$H$_{22}$Cl$_2$O$_4$: Calc.: C, 59.23; H, 5.76; Found: C, 59.25; H, 5.82.

EXAMPLE 2

4-[(6,7-Dichloro-2-cyclopentyl-2-ethyl-2,3-dihydro-1-oxo-1H-inden-5-yl)oxy]butanoic Acid

Step A:
6,7-Dichloro-2-cyclopentyl-2-ethyl-2,3-dihydro-5-methoxy-1H-inden-1-one By following substantially the procedure described in Example 1, Step D, but substituting for the methyl iodide therein described an equimolar quantity of ethyl iodide and substituting a mixture of equal volumes of dimethylformamide and toluene for the 1,2-dimethoxyethane used therein, there is obtained 6,7-Dichloro-2-cyclopentyl-2-ethyl-2,3-dihydro-5-methoxy-1H-inden-1-one, which melts at 163° C.

Analysis for C$_{17}$H$_{20}$Cl$_2$O$_2$ Calc.: C, 62.39; H, 6.16; Found: C, 62.35; H, 6.36.

Step B:
6,7-Dichloro-2-cyclopentyl-2-ethyl-2,3-dihydro-5-hydroxy-1H-inden-1-one By following substantially the procedure described in Example 8, Step A, but substituting for the (+)[(6,7-dichloro-2-cyclopentyl-2,3-dihydro-2-methyl-1-oxo-1H-inden-5-yl)oxy]acetic acid therein described, an equimolar quantity of 6,7-dichloro-2-cyclopentyl-2,3-dihydro-2-ethyl-5-methoxy-1H-inden-1-one there is obtained 6,7-dichloro-2-cyclopentyl-2-ethyl-2,3-dihydro-5-hydroxy-1H-inden-1-one which is used in Step C without further purification.

Step C:
4-[(6,7-Dichloro-2-cyclopentyl-2-ethyl-2,3-dihydro-1-oxo-1H-inden-5-yl)oxy]butanoic Acid By following substantially the procedure described in Example 1, Step F, but substituting for the 6,7-dichloro-2-cyclopentyl-2,3-dihydro-5-hydroxy-2-methyl-1H-inden-1-one an equimolar quantity of 6,7-dichloro-2-cyclopentyl-2-ethyl-2,3-dihydro-5-hydroxy-1H-inden-1-one therein described, there is obtained 4-[(6,7-dichloro-2-cyclopentyl-2-ethyl-2,3-dihydro-1-oxo-1H-inden-5-yl)oxy]butanoic acid which melts at 189°–193° C.

Analysis for C$_{20}$H$_{24}$Cl$_2$O$_4$ Calc.: C, 60.16; H, 6.06; Found: C, 59.91; H, 6.13.

EXAMPLE 3

4-[(6,7-Dichloro-2-cyclopentyl-2,3-dihydro-1-oxo-2-propyl-1H-inden-5-yl)oxy]butanoic Acid

Step A:
6,7-Dichloro-2-cyclopentyl-2,3-dihydro-2-propyl-5-methoxy-1H-inden-1-one By following substantially the procedure described in Example 2, Step A, but substituting for the ethyl iodide therein described, an equimolar quantity of propyl iodide there is obtained 6,7-dichloro-2-cyclopentyl-2,3-dihydro-2-propyl-5-methoxy-1H-inden-1-one.

Step B:
6,7-Dichloro-2-cyclopentyl-2,3-dihydro-5-hydroxy-2-propyl-1H-inden-1-one By following substantially the procedure described in Example 2, Step B, but substituting for the 6,7-dichloro-2-cyclopentyl-2,3-dihydro-5-methoxy-2-ethyl-1H-inden-1-one therein described, an equimolar quantity of 6,7-dichloro-2-cyclopentyl-2,3-dihydro-5-methoxy-2-propyl-1H-inden-1-one there is obtained 6,7-dichloro-2-cyclopentyl-2,3-dihydro-5-hydroxy-2-propyl-1H-inden-1-one, which is used in Step C without further purification.

Step C:
4-[(6,7-dichloro-2-cyclopentyl-1-oxo-2-propyl-1H-inden-5-yl)oxy]butanoic acid By following substantially the procedure described in Example 2, Step C, but substituting for the 6,7-dichloro-2-cyclopentyl-2,3-dihydro-5-hydroxy-2-ethyl-1H-inden-1-one, an equimolar quantity of 6,7-dichloro-2-cyclopentyl-2,3-dihydro-5-hydroxy-2-propyl-1H-inden-1-one therein described, there is obtained 4-[(6,7-dichloro-2-cyclopentyl-1-oxo-2-propyl-1H-inden-5-yl)oxy]butanoic acid, which melts at 140°–141° C.

Analysis for C$_{21}$H$_{26}$Cl$_2$O$_4$ Calc.: C, 61.02; H, 6.34; Found: C, 61.05; H, 6.53.

EXAMPLE 4

4-[(2-Butyl-6,7-dichloro-2-cyclopentyl-2,3-dihydro-1-oxo-1H-inden-5-yl)oxy]butanoic Acid

Step A:
2-Butyl-6,7-dichloro-2-cyclopentyl-2,3-dihydro-5-methoxy-1H-inden-1-one By following substantially the procedure described in Example 2, Step A, but substituting for the ethyl iodide therein described, an equimolar quantity of butyl iodide, there is obtained 2-butyl-6,7-dichloro-2-cyclopentyl-2,3-dihydro-5-methoxy-1H-inden-1-one.

Step B:
2-Butyl-6,7-dichloro-2-cyclopentyl-2,3-dihydro-5-hydroxy-1H-inden-1-one By following substantially the procedure described in Example 2, Step B, but substituting for the 6,7-dichloro-2-cyclopentyl-2-ethyl-2,3-dihydro-5-methoxy-1H-inden-1-one therein described, an equimolar quantity of 6,7-dichloro-2-cyclopentyl-2,3-dihydro-5-methoxy-1H-inden-1-one there is obtained 2-butyl-6,7-dichloro-2-cyclopentyl-2,3-dihydro-5-hydroxy-1H-inden-1-one, which is used in Step C without further purification.

Step C:
4-[(2-Butyl-6,7-dichloro-2-cyclopentyl-2,3-dihydro-1-oxo-1H-inden-5-yl)oxy]butanoic acid By following substantially the procedure described in Example 2, Step C, but substituting for the 6,7-dichloro-2-cyclopentyl-2-ethyl-2,3-dihydro-5-hydroxy-1H-inden-1-one, an equimolar quantity of 2-butyl-6,7-dichloro-2-cyclopentyl-2,3-dihydro-5-hydroxy-1H-inden-1-one, therein described, there is obtained 4-[(2-butyl-6,7-dichloro-2-cyclopentyl-2,3-dihydro-1-oxo-1H-inden-5-yl)oxy]-butanoic acid, which melts at 156.5°–159° C.

Analysis for $C_{22}H_{28}Cl_2O_4$ Calc.: C, 61.83; H, 6.61; Found: C, 61.64; H, 6.73.

EXAMPLE 5

4-[6,7-Dichloro-2-cyclopentyl-2,3-dihydro-1-oxo-2-pentyl-1H-inden-5-yl)oxy]butanoic Acid

Step A:
6,7-Dichloro-2-cyclopentyl-2,3-dihydro-5-methoxy-2-pentyl-1H-inden-1-one By following substantially the procedure described in Example 2, Step A, but substituting for the ethyl iodide therein described, an equimolar quantity of pentyl iodide, there is obtained 6,7-dichloro-2-cyclopentyl-2,3-dihydro-5-methoxy-2-pentyl-1H-inden-1-one, which is used in Step B without further purification.

Step B:
6,7-Dichloro-2-cyclopentyl-2,3-dihydro-5-hydroxy-2-pentyl-1H-inden-1-one By following substantially the procedure described in Example 2, Step B, but substituting for the 6,7-dichloro-2-cyclopentyl-2,3-dihydro-5-methoxy-2-methyl-1H-inden-1-one-therein described, an equimolar quantity of 6,7-dichloro-2-cyclopentyl-2,3-dihydro-5-methoxy-2-pentyl-1H-inden-1-one there is obtained 6,7-dichloro-2-cyclopentyl-2,3-dihydro-5-hydroxy-2-pentyl-1H-inden-1-one which is used in Step C without further purification.

Step C:
4-[(6,7-Dichloro-2-cyclopentyl-2,3-dihydro-1-oxo-2-pentyl-1H-inden-5-yl)oxy]butanoic Acid By following substantially the procedure described in Example 2, Step C, but substituting for the 6,7-dichloro-2-cyclopentyl-2-ethyl-2,3-dihydro-5-hydroxy-1H-inden-1-one an equimolar quantity of 6,7-dichloro-2-cyclopentyl-2,3-dihydro-5-hydroxy-2-pentyl-1H-inden-1-one therein described, there is obtained 4-[(6,7-dichloro-2-cyclopentyl-2,3-dihydro-1-oxo-2-pentyl-1H-inden-5-yl)oxy]butanoic acid.

EXAMPLE 6

4-[(6,7-Dichloro-2-cyclopentyl-2-hexyl-2,3-dihydro-1-oxo-1H-inden-5-yl)oxy]butanoic Acid

Step A:
6,7-Dichloro-2-cyclopentyl-2,3-dihydro-2-hexyl-5-methoxy-1H-inden-1-one By following substantially the procedure described in Example 2, Step A, but substituting for the ethyl iodide therein described, an equimolar quantity of hexyl iodide there is obtained 6,7-dichloro-2-cyclopentyl-2-hexyl-2,3-dihydro-5-methoxy-1H-inden-1-one.

Step B:
6,7-Dichloro-2-cyclopentyl-2-hexyl-2,3-dihydro-5-hydroxy-1H-inden-1-one By following substantially the procedure described in Example 2, Step B, but substituting for the 6,7-dichloro-2-cyclopentyl-2-ethyl-2,3-dihydro-5-methoxy-1H-inden-1-one therein described, an equimolar quantity of 6,7-dichloro-2-cyclopentyl-2-hexyl-2,3-dihydro-5-methoxy-1H-inden-1-one there is obtained 6,7-dichloro-2-cyclopentyl-2-hexyl-2,3-dihydro-5-hydroxy-1H-inden-1-one, which is used in Step C without further purification.

Step C:
4-[(6,7-dichloro-2-cyclopentyl-2-hexyl-2,3-dihydro-1-oxo-2-hexyl-1H-inden-5-yl)oxy]butanoic acid By following substantially the procedure described in Example 2, Step C, but substituting for the 6,7-dichloro-2-cyclopentyl-2-ethyl-2,3-dihydro-5-hydroxy-1H-inden-1-one, an equimolar quantity of 6,7-dichloro-2-cyclopentyl-2-hexyl-2,3-dihydro-5-hydroxy-1H-inden-1-one therein described, there is obtained 4-[(6,7-dichloro-2-cyclopentyl-2-hexyl-2,3-dihydro-1-oxo-1H-inden-5-yl)oxy]butanoic acid.

EXAMPLE 7

Ethyl 4-[(6,7-dichloro-2-cyclopentyl-2,3-dihydro-2-methyl-1-oxo-1H-inden-5-yl)oxy]butanoate To a suspension of 4-[(6,7-dichloro-2-cyclopentyl-2,3-dihydro-2-methyl-1-oxo-1H-inden-5-yl)-oxy]-butanoic acid (0.5 g, 0.0012 mole) in absolute ethanol (50 ml) is added conc. sulfuric acid and the mixture is refluxed for 1 hr., treated with 3 Å molecular sieves and stirred at 25° for 18 hours. The reaction mixture is treated with more conc. sulfuric acid (0.2 ml) refluxed for 1 hr, filtered and treated with solid potassium carbonate. The ethanol is distilled at reduced pressure to give ethyl 4-[(6,7-dichloro-2-cyclopentyl-2,3-dihydro-2-methyl-1-oxo-1H-inden-5-yl)oxy]butanoate which is purified by chromatography on silica gel eluted with methylene chloride-tetrahydrofuran (100:1).

Analysis for $C_{21}H_{26}Cl_2O$ Calc.: C, 61.02; H, 6.34; Found: C, 60.93; H, 6.39.

The product also can be prepared by mixing 4-[(6,7-dichloro-2-cyclopentyl-2,3-dihydro-2-methyl-1-oxo-1H-inden-5-yl)oxy]butanoic acid (0.5 g, 0.0012 mole) with ethanol (0.0024 mole) in methylene chloride and adding dicyclohexylcarbodiimide (0.26 g, 0.0013 mole), filtering and purifying by chromatography as described above.

EXAMPLE 8

(+) Sodium 4-[(6,7-dichloro-2-cyclopentyl-2,3-dihydro-2-methyl-1-oxo-1H-inden-5-yl)oxy]butanoate hemisemihydrate

Step A: (+)
6,7-Dichloro-2-cyclopentyl-2,3-dihydro-5-hydroxy-2-methyl-1H-inden-1-one A 19.5 g. sample of (+) [(6,7-dichloro-2-cyclopentyl-2,3-dihydro-2-methyl-1-oxo-1H-inden-5-yl)-oxy]acetic acid is added to stirred molten (190° C.) pyridine hydrochloride, stirred for 1 hour then poured into ice water (800 ml). The (+)6,7-dichloro-2-cyclopentyl-2,3-dihydro--5-hydroxy-2-methyl-1H-inden-1-one, which separates is filtered, rinsed with water and dried.

Step B: (+) Sodium
4-[(6,7-dichloro-2-cyclopentyl-2,3-dihydro-2-methyl-1-oxo-1H-inden-5-yl)oxy]butanoate hemisemihydrate A mixture of (+) 6,7-dichloro-2-cyclopentyl-2,3-dihydro-5-hydroxy-2-methyl-1H-inden-1-one (14.25 g, 0.046 mole) potassium carbonate (12.5 g, 0.09 mole) and ethyl 4-bromobutanoate (17.5 g, 0.08 mole) in DMF (150 ml) is stirred at 55° C. for 4 hours then poured into ice water and extracted with ether, washed with water and the ether evaporated at reduced pressure. The residual oil is dissolved in acetic acid (150 ml) and 5% hydrochloric acid (50 ml), heated at 95° C. for 2½ hours, cooled and treated with ie (50 g) to give 17.65 g of (+)[(6,7-dichloro-2-cyclopentyl-2,3-dihydro-2-methyl-1-oxo-1H-inden-5-yl)-oxy]butanoic acid which melts at 75°-77° C. [α]$_D^{25}$ (C=2, acetone)= +36.8°.

The butanoic acid is dissolved in water (800 ml) containing a slight excess of N-methylpiperazine, filtered and treated with ice and slight excess of 10N sodium hydroxide. The (+) sodium 4-[(6,7-dichloro-2-cyclopentyl-2,3-dihydro-2-methyl-1-oxo-1H-inden-5-yl)oxy]-butanoate hemisemihydrate, which separates melts at 204°-205° C. after recrystallization from water.

Analysis for C$_{19}$H$_{21}$Cl$_2$NaO$_4$(¼H$_2$O) Calc.: C, 55.41; H, 5.26; Cl, 17.22; Found: C, 55.01; H, 5.26; Cl, 17.50.

EXAMPLE 9

(+)
4-[(2-Butyl-6,7-dichloro-2-cyclopentyl-2,3-dihydro-1-oxo-1H-inden-5-yl)oxy]butanoic acid Step A:
(+)[(2-Butyl-6,7-dichloro-2-cyclopentyl-2,3-dihydro-1-oxo-1H-inden-5-yl)oxy]acetic acid Equimolar amounts of racemic [(2-butyl-6,7-dichloro-2-cyclopentyl-2,3-dihydro-1-oxo-1H-inden-5-yl)oxy]acetic acid (26.1 g, 0.065 mole) and (+) cinchonine (19.2, 0.065 ml) are dissolved in dimethylformamide (400 ml) at 110° C., then allowed to cool to ambient temperature. The salt which precipitates (27 g) is purified by ten crystallization from dimethylformamide. This diastereomeric salt (10.7 g) is partitioned between water and ether and acidified with 6N HCl to liberate the ether soluble free acid. The ether extracts are washed with dilute aqueous HCl followed by water and then dried over anhydrous magnesium sulfate. After filtration and concentration in vacuo, there is obtained 5.6 g of (+)[(2-butyl-6,7-dichloro-2-cyclopentyl-2,3-dihydro-1-oxo-1H-inden-5-yl)oxy]acetic acid which melts at 173°-174° C., [α]$_D^{24}$+19.1° (C=5, ethanol).

Step B: (+)
2-Butyl-6,7-dichloro-2-cyclopentyl-2,3-dihydro-5-hydroxy-1H-inden-1-one By following substantially the procedure in Example 8, Step A, but substituting for (+)[(6,7-dichloro-2-cyclopentyl-2,3-dihydro-2-methyl-1-oxo-1H-inden-5-yl)oxy]acetic acid an equimolar quantity of (+)[(2-butyl-6,7-dichloro-2-cyclopentyl-2,3-dihydro-1-oxo-1H-inden-5-yl)oxy]acetic acid, there is obtained (+)2-butyl-6,7-dichloro-2-cyclopentyl-2,3-dihydro-5-hydroxy-1H-inden-1-one which is used in Step C without further purification.

Step C: (+)
4-[(2-Butyl-6,7-dichloro-2-cyclopentyl-2,3-dihydro-1-oxo-1H-inden-5-yl)oxy]butanoic acid By following substantially the procedure in Example 8, Step B, but substituting for (+) 6,7-dichloro-2-cyclopentyl-2,3-dihydro-5-hydroxy-2-methyl-1H-inden-1-one an equimolar quantity of (+) 2-butyl-6,7-dichloro-2-cyclopentyl-2,3-dihydro-5-hydroxy-1H-inden-1-one described therein, there is obtained (+) 4-[(2-butyl-6,7-dichloro-2-cyclopentyl-2,3-dihydro-1-oxo-1H-inden-5-yl)oxy]butanoic acid which melts at 139°-139.5° C., [α]$_D^{25}$+18.4° (C=5, ethanol).

Analysis for C$_{22}$H$_{28}$Cl$_2$O$_4$: Calc.: C, 61.83; H, 6.60; Cl, 16.59; Found: C, 61.96; H, 6.78; Cl, 16.61.

EXAMPLE 10

(−)
4-[(2-Butyl-6,7-dichloro-2-cyclopentyl-2,3-dihydro-1-oxo-1H-inden-5-yl)oxy]butanoic acid Step A:
(−)[(2-Butyl-6,7dichloro-2-cyclopentyl-2,3-dihydro-1-oxo-1H-inden-5-yl)oxy]acetic acid The initial filtrate from Example 9, Step A, which is enriched with the (−) enantiomer and is in the form of the cinchonine salt is partitioned between water and ether, is acidified with 6N hydrochloric acid to liberate the ether soluble free acid. By following substantially the procedure in Example 9, Step A, but substituting (−) cinchonidine for (+)cinchonine there is obtained (−)[(2-butyl-6,7-dichloro-2-cyclopentyl-2,3-dihydro-1-oxo-1H-inden-5-yl)oxy]acetic acid which melts at 172°-173.5° C., [α]$_D^{24}$ − 18.6° (C=5, ethanol).

Step B: (−)
2-Butyl-6,7-dichloro-2-cyclopentyl-2,3-dihydro-5-hydroxy-1H-inden-1-one By following substantially the procedure in Example 8, Step A, but substituting for (+) 6,7-dichloro-2-cyclopentyl-2,3-dihydro-2-methyl-1-oxo-1H-inden-5-yl)oxy]acetic acid an equimolar quantity of (−) [(2-butyl-6,7-dichloro-2-cyclopentyl-2,3-dihydro-1-oxo-1H-inden-5-yl)oxy]acetic acid, there is obtained (−) 2-butyl-6,7-dichloro-2-cyclopentyl-2,3-dihydro-5-hydroxy-1H-inden-1-one which is used in Step C without further purification.

Step C: (−)
4-[(2-Butyl-6,7-dichloro-2-cyclopentyl-2,3-dihydro-1-oxo-1H-inden-5-yl)oxy]butanoic acid By following substantially the procedure in Example 8, Step B, but substituting for (+) 6,7-dichloro-2-cyclopentyl-2,3-dihydro-5-hydroxy-2-methyl-1H-inden-1-one, an equimolar quantity of (−) 2-butyl-6,7-dichloro-2-cyclopentyl-2,3-dihydro-5-hydroxy-1H-inden-1-one therein described, there is obtained (−) 4-[(2-butyl-6,7-dichloro-2-cyclopentyl-2,3-dihydro-1-oxo-1H-inden-5-yl)oxy]butanoic acid which melts at 139°-139:5° C., [α]$_D^{25}$ − 17.7° (C=5, ethanol).

Analysis for: C$_{22}$H$_{28}$Cl$_2$O$_4$ Calc.: C, 61.83; H, 6.60; Cl, 16.59; Found: C, 61.92; H, 6.83; Cl, 16.44.

EXAMPLE 11

1-Carboxy-1-methylethyl (+)
4-[6,7-dichloro-2-cyclopentyl-2,3-dihydro-2-methyl-1-oxo-1H-inden-5-yl)oxy]butanoate Step A:
1-{(+)[6,7-dichloro-2-cyclopentyl-2,3-dihydro-2-methyl-1-oxo-1H-inden-5-yl)oxy]-butanoyl}imidazole (+) [(6,7-Dichloro-2-cyclopentyl-2,3-dihydro-2-methyl-1-oxo-1H-inden-yl)oxy]butanoic acid (Example 8, Step B) (0.77 g, 0.002 mole) is suspended in dry tetrahydrofuran (20 ml) and cooled to 0° C. A solution of 1,1'-carbonyldiimidazole (0.32 g, 0.002 mole) in teterahydrofuran (5 ml) is added. The solution of 1-{(+)-4-[(6,7-dichloro-2-cyclopentyl-2,3-dihydro-2-methyl-1-oxo-1H-inden-5-yl)oxy]butanoyl}imidazole that is formed is used in the next step without isolation.

Step B: 1-Carboxy-1-methylethyl (+) 4-[(6,7-dichloro-2-cyclopentyl-2,3-dihydro-2-methyl-1-oxo-1H-inden-5yl)oxy]butanoate To the solution of 1-{(+) 4-[(6,7-dichloro-2-cyclopentyl-2,3-dihydro-2-methyl-1-oxo-1H-inden-5-yl)oxy]-butanoyl}imidazole (0.002 mole) prepared in Step A at 0° C. is added with stirring 2-hydroxyisobutyric acid (0.21 g., 0.002 mole) and a catalytic amount of sodium hydride (10 mg). After stirring overnight at the ambient temperature, the colorless reaction mixture is concentrated in vacuo at 50° C. The resultant yellow liquid is chromatographed using a silica-gel (60 gm) column and eluted with a mixture of methylene chloride, tetrahydrofuran and acetic acid (100/2/1 v.v.v) to give analytically pure 1-carboxy-1-methylethyl (+) 4-[(6,7-dichloro-2-cyclopentyl-2,3-dihydro-2-methyl-1-oxo-1H-inden-5-yl)oxy]butanoate.

EXAMPLE 12

1-Carboxy-1-methylethyl (+) [(2-butyl-6,7-dichloro-2-cyclopentyl-2,3-dihydro-1-oxo-1H-inden-5-yl)oxy]butanoate

Step A:
1-{(+)4-[(2-butyl-6,7-dichloro-2-cyclopentyl-2,3-dihydro-1-oxo-1H-inden-5-yl)oxy]butanoyl}-imidazole By substituting an equimolar amount of (+) 4-[2-butyl-6,7-dichloro-2-cyclopentyl-2,3-dihydro-1-oxo-1H-inden-5-yl)oxy]butanoic acid for the (+) 4-[(6,7-dichloro-2-cyclopentyl-2,3-dihydro-2-methyl-1-oxo-1H-inden-5-yl)oxy]butanoic acid used in Example 11A and conducting the reaction as described in Example 11A, there is obtained 1-{(+)4-[(2-butyl-6,7-dichloro-2-cyclopentyl-2,3-dihydro-1-oxo-1H-inden-5-yl)oxy]-butanoyl}imidazole.

Step B: 1-Carboxy-1-methylethyl (+) 4-[(2-butyl-6,7-dichloro-2-cyclopentyl-2,3-dihydro-1-oxo-1H-inden-5-yl)oxy]butanoate By substituting an equimolar amount of 1-(+){4-[(2-butyl-6,7-dichloro-2-cyclopentyl-2,3-dihydro-1-oxo-1H-inden-5-yl)oxy]butanoyl}imidazole for the 1-{(+) 4-[(6,7-dichloro-2-cyclopentyl-2,3-dihydro-2-methyl-1-oxo-1H-inden-5-yl)oxy]butanoyl}imidazole used in Example 11B and conducting the reaction as described in Example 11B, there is obtained 1-carboxy-1-methylethyl (+) 4-[(2-butyl-6,7-dichloro-2-cyclopentyl-2,3-dihydro-1-oxo-1H-inden-5-yl)oxy]butanoate.

EXAMPLE 13

1-Carboxy-1-methylethyl (−) 4-[(2-butyl-6,7-dichloro-2-cyclopentyl-2,3-dihydro-1-oxo-1H-inden-5-yl)oxy]-butanoate

Step A: 1-{(−) 4-[(2-Butyl-6,7-dichloro-2-cyclopentyl-2,3-dihydro-1-oxo-1H-inden-5-yl)oxy]butanoyl}imidazole By substituting an equimolar amount of (−) 4-[(6,7-dichloro-2-cyclopentyl-2,3-dihydro-1-oxo-1H-inden-5-yl)oxy]butanoic acid for the (+) 4-[(2-butyl-6,7-dichloro-2-cyclopentyl-2,3-dihydro-2-methyl-1-oxo-1H-inden-5-yl)oxy]butanoic acid used in Example 11A and conducting the reaction as described in Example 11A there is obtained 1-{(−) [(2-butyl-6,7-dichloro-2-cyclopentyl-2,3-dihydro-1-oxo-1H-inden-5-yl)oxy]-butanoyl}imidazole.

Step B: 1-Carboxy-1-methylethyl (−) [(2-butyl-6,7-dichloro-2-cyclopently-2,3-dihydro-1-oxo-1H-inden-5-yl)oxy]butanoate By substituting an equimolar amount of 1-{(−) 4-[2-butyl-6,7-dichloro-2-cyclopentyl-2,3-dihydro-1-oxo-1H-inden-5-yl)oxy]butanoyl}imidazole for the 1-{(+) 4-[(6,7-dichloro-2-cyclopentyl-2,3-dihydro-2-methyl-1-oxo-1H-inden-5-yl)oxy]butanoyl}-imidazole used in Example 11B and conducting the reaction as described in Example 11B, there is obtained 1-carboxy-1-methylethyl (−) 4-[(2-butyl-6,7-dichloro-2-cyclopentyl-2,3-dihydro-2-oxo-1H-inden-5-yl)oxy]butanoate.

The compounds of formulae I are utilized by formulating them in a composition such as tablet, capsule or elixir for oral administration. Sterile solutions or suspensions can be used for parenteral administration. About 70 μg to 150 mg of a compound or mixture of compounds of formulae I or a physiologically acceptable salt, ester, or amide is compounded with a physiologically acceptable vehicle, carrier, excipient, binder, preservative, stabilizer, flavor, etc. in a unit dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are included to illustrate the preparation of representative dosage forms.

EXAMPLE 14

Dry-filled capsules containing 25 mg of active ingredient per capsule

|  | Per Capsule |
|---|---|
| (+)4-[6,7-dichloro-2-cyclopentyl-2,3-dihydro-2-methyl-1-oxo-1H—inden-5-yl)oxy]-butanoic acid | 25 mg |
| Lactose | 124 mg |
| Magnesium Stearate | 1 mg |
| Capsule (Size No. 1) | 200 mg |

The (+) 4-[6,7-dichloro-2-cyclopentyl-2,3-dihydro-2-methyl-1-oxo-1H-inden-5-yl)oxy]butanoic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 15

Dry-filled capsules containing 25 mg of active ingredient per capsule

|  | Per Capsule |
| --- | --- |
| (+)4-[(2-butyl-6,7-dichloro-2-cyclopentyl-2,3-dihydro-1-oxo-1H—inden-5-yl)oxy]butanoic acid | 25 mg |
| Lactose | 124 mg |
| Magnesium Stearate | 1 mg |
| Capsule (Size No. 1) | 200 mg |

The (+) 4-[(2-butyl-6,7-dichloro-2-cyclopentyl-2,3-dihydro-1-oxo-1H-inden-5-yl)oxy]butanoic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 16

Dry-filled capsules containing 25 mg of active ingredient per capsule

|  | Per Capsule |
| --- | --- |
| (−)4-[(2-butyl-6,7-dichloro-2-cyclopentyl-2,3-dihydro-1-oxo-1H—inden-5-yl)oxy]butanoic acid | 25 mg |
| Lactose | 124 mg |
| Magnesium Stearate | 1 mg |
| Capsule (Size No. 1) | 200 mg |

The (−) 4-[(2-butyl-6,7-dichloro-2-cyclopentyl-2,3-dihydro-1-oxo-1H-inden-5-yl)oxy]butanoic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other compounds of this invention.

EXAMPLE 17

Parenteral Solution of the sodium salt of (+) 4-[(6,7-dichloro-2-cyclopentyl-2,3-dihydro-2-methyl-1-oxo-1H-inden-5-yl)oxy]butanoic acid 100 mg. of (+) 4-[(6,7-dichloro-2-cyclopentyl-2,3-dihydro-2-methyl-1-oxo-1H-inden-5-yl)oxy]butanoic acid is dissolved in 3 ml. of 0.1N-sodium hydrogen carbonate solution. The solution is made up to 10 ml. with water and sterilized by filtration.

EXAMPLE 18

Parenteral Solution of the sodium salt of (−) 4-[(2-butyl-6,7-dichloro-2-cyclopentyl-2,3-dihydro-1-oxo-1H-inden-5-yl)oxy]butanoic acid 100 mg. of (−) 4-[(2-butyl-6,7-dichloro-2-cyclopentyl-2,3-dihydro-1-oxo-1H-inden-5-yl)oxy]butanoic acid is dissolved in 3 ml. of 0.1N sodium hydrogen carbonate solution. The solution is diluted with water to a volume of 40 ml. and sterilized by filtration.

EXAMPLE 19

Parenteral Solution of the sodium salt of 1-carboxy-1-methylethyl (+) 4-[(6,7-dichloro-2-cyclopentyl-2,3-dihydro-2-methyl-1-oxo-1H-inden-5-yl)oxy]butanoate 100 mg. of 1-carboxy-1-methyl (+) 4-[(6,7-dichloro-2-cyclopentyl-2,3-dihydro-2-methyl-1-oxo-1H-inden-5-yl)oxy]butanoate is dissolved in 3 ml. of 0.1N sodium hydrogen carbonate solution. The solution is diluted with water to a volume of 40 ml. and sterilized by filtration.

EXAMPLE 20

Parenteral Solution of the sodium salt of 1-carboxy-1-methylethyl (−) 4-[(2-butyl-6,7-dichloro-2-cyclopentyl-2,3-dihydro-1-oxo-1H-inden-5-yl)oxy]butanoate 100 mg. of 1-carboxy-1-methylethyl (−) 4-[(2-butyl-6,7-dichloro-2-cyclopentyl-2,3-dihydro-1-oxo-1H-inden-5-yl)oxy]butanoate is dissolved in 3 ml. of 0.1N sodium hydrogen carbonate. The solution is diluted with water and sterilized by filtration.

EXAMPLE 21

Parenteral Solution of the sodium salt of 1-carboxy-1-methylethyl (+) 4-[(2-butyl-6,7-dichloro-2-cyclopentyl-2,3-dihydro-1-oxo-1H-inden-5-yl)oxy]butanoate 100 mg. of (+) 4-[(2-butyl-6,7-dichloro-2-cyclopentyl-2,3-dihydro-1-oxo-1H-inden-5-yl)oxy]butanoate is dissolved in 3 ml. of 0.1N sodium hydrogen carbonate solution. The solution is diluted with water to a volume of 40 ml. and sterilized by filtration.

EXAMPLE 22

Parenteral Solution of the sodium salt of (+) 4-[(2-butyl-6,7-dichloro-2-cyclopentyl-2,3-dihydro-1-oxo-1H-inden-5-yl)oxy]butanoic acid 100 mg. of (+) 4-[(2-butyl-6,7-dichloro-2-cyclopentyl-2,3-dihydro-1-oxo-1H-inden-5-yl)oxy]butanoic acid is dissolved in 3 ml. of 0.1N sodium hydrogen carbonate. The solution is diluted with water to a volume of 10 ml. and sterilized by filtration.

What is claimed is:

1. A compound of the formula

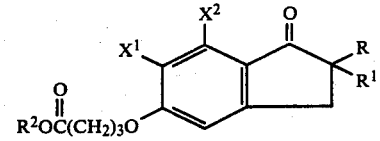

wherein
$X^1$ and $X^2$ are halo;

R is lower alkyl of from 1 to 6 carbon atoms;

$R^1$ is lower alkyl of 1 to 4 carbon atoms, cycloalkyl of 3 to 6 carbon atoms, lowercycloalkylloweralkyl of 4 to 7 carbon atoms and phenyl;

$R^2$ is hydrogen or lower alkyl of 1 to 6 carbon atoms, and carboxy lower alkyl of 2 to 6 carbon atoms; and the pharmaceutically acceptable salts thereof.

2. A compound according to claim 1 wherein $X^1$ and $X^2$ are chloro.

3. A compound according to claim 2 wherein R is cyclopentyl.

4. A compound according to claim 3 wherein $R^2$ is H.

5. A compound according to claim 4 wherein $R^1$ is methyl, that is 4-[(6,7-dichloro-2-cyclopentyl-2,3-dihydro-2-methyl-1-oxo-1H-inden-5-yl)oxy]butanoic acid.

6. A compound according to claim 5 which is the (+) enantiomer.

7. A compound according to claim 4 wherein $R^1$ is ethyl, that is, 4-[(6,7-dichloro-2-cyclopentyl-2-ethyl-2,3-dihydro-1-oxo-1H-inden-5-yl)oxy]butanoic acid.

8. A compound according to claim 4 wherein $R^1$ is propyl, that is, 4-[(6,7-dichloro-2-cyclopentyl-2,3-dihydro-1-oxo-2-propyl-1H-inden-5-yl)oxy]butanoic acid.

9. A compound according to claim 4 wherein $R^1$ is butyl, that is, 4-[(2-butyl-6,7-dichloro-2-cyclopentyl-2,3-dihydro-1-oxo-1H-inden-5-yl)oxy]butanoic acid.

10. A compound according to claim 9 which is the (+) enantiomer.

11. A compound according to claim 9 which is the (−) enantiomer.

12. A compound according to claim 3 wherein $R^1$ is methyl and $R^2$ is 1-carboxy-1-methylethyl, that is, 1-carboxy-1-methylethyl (+) 4-[(6,7-dichloro-2-cyclopentyl-2,3-dihydro-2-methyl-1-oxo-1H-inden-5-yl)oxy]butanoate.

13. A compound according to claim 4 wherein R is butyl and $R^2$ is 1-carboxy-1-methylethyl, that is, 1-carboxy-1-methylethyl (+) 4-[(2-butyl-6,7-dichloro-2-cyclopentyl-2,3-dihydro-1-oxo-1H-inden-5-yl)oxy]-butanoate.

14. A compound according to claim 4 wherein $R^1$ is butyl and $R^2$ is 1-carboxy-1-methylethyl, that is, (−) 4-[(2-butyl-6,7-dichloro-2-cyclopentyl-2,3-dihydro-1-oxo-1H-inden-5-yl)oxy]butanoate.

15. A method of treating persons with gray matter edema which comprises administering to such a person an effctive amount of a compound of the formulae:

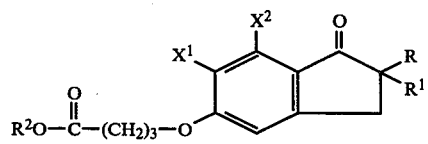

where $X^1$ and $X^2$ are halo;

R is lower alkyl of from 1 to 6 carbon atoms;

$R^1$ is lower alkyl of 1–4 carbon atoms, cycloalkyl of 3 to 6 carbon atoms, lowercycloalkylloweralkyl of 4 to 7 carbon atoms and phenyl;

$R^2$ is hydrogen or lower alkyl, and carboxy lower alkyl of 2 to 6 carbon atoms; or the pharmaceutically acceptable salts thereof.

16. The method of claim 15 wherein $X^1$ and $X^2$ are chloro.

17. The method of claim 16 where $R^2$ is hydrogen.

18. The method of claim 17 where R is cyclopentyl.

19. The method of claim 18 where $R^1$ is lower alkyl.

20. The method of claim 19 where $R^1$ is methyl.

21. The method of claim 20 where the compound is the (+) enantiomer.

22. The method of claim 19 where R is ethyl.

23. The method of claim 19 where $R^1$ is propyl.

24. The method of claim 19 where $R^1$ is butyl.

25. The method of claim 24 where the compound is the (+) enantiomer.

26. The method of claim 24 where the compound is the (−) enantiomer.

27. The method of claim 16 where R is cyclopentyl, $R^1$ is methyl and $R^2$ is 1-carboxy-1-methylethyl.

28. The method of claim 27 where the compound is the (+) enantiomer.

29. The method of claim 16 where R is cyclopentyl, $R^1$ is butyl and $R^2$ is 1-carboxy-1-methylethyl.

30. The method of claim 29 where the compound is the (−) enantiomer.

31. The method of claim 29 where the compound is the (+) enantiomer.

32. A composition for treating gray matter edema which comprises a carrier and an effective amount of the formula:

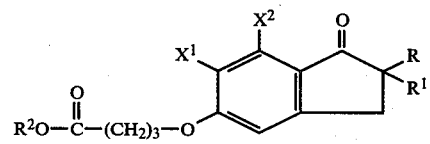

where $X^1$ and $X^2$ are halo;

R is lower alkyl of from 1 to 6 carbon atoms;

$R^1$ is lower alkyl of 1 to 4 carbon atoms, cycloalkyl of 3 to 6 carbon atoms, lowercycloalkylloweralkyl of 4 to 7 carbon atoms and phenyl;

$R^2$ is hydrogen or lower alkyl, and carboxy lower alkyl of 2 to 6 carbon atoms;

or the pharmaceutically acceptable salts thereof.

* * * * *